United States Patent
de Villiers et al.

(10) Patent No.: US 8,090,428 B2
(45) Date of Patent: *Jan. 3, 2012

(54) SPINAL MIDLINE INDICATOR

(75) Inventors: Malan de Villiers, Wapadrand (ZA);
Ulrich R. Hahnle, Saxonwold (ZA)

(73) Assignee: SpinalMotion, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/616,697

(22) Filed: Nov. 11, 2009

(65) Prior Publication Data

US 2010/0049040 A1    Feb. 25, 2010

Related U.S. Application Data

(63) Continuation of application No. 11/187,733, filed on Jul. 21, 2005, now Pat. No. 7,637,913, which is a continuation of application No. PCT/IB2004/000170, filed on Jan. 26, 2004.

(30) Foreign Application Priority Data

Jan. 31, 2003 (ZA) .................................. 2003/0874

(51) Int. Cl.
*A61F 2/44* (2006.01)
*A61B 17/56* (2006.01)
*A61B 5/05* (2006.01)

(52) U.S. Cl. ........ 600/426; 600/424; 606/99; 623/17.16
(58) Field of Classification Search ........................ None
See application file for complete search history.

(56) References Cited

U.S. PATENT DOCUMENTS

| | | |
|---|---|---|
| 3,486,505 A | 12/1969 | Morrison |
| 3,867,728 A | 2/1975 | Stubstad et al. |
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buttner-Janz et al. |

(Continued)

FOREIGN PATENT DOCUMENTS

DE    3023353 A1    9/1981

(Continued)

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

(Continued)

*Primary Examiner* — Long V. Le
*Assistant Examiner* — Lawrence Laryea
(74) *Attorney, Agent, or Firm* — Wilson Sonsini Goodrich & Rosati

(57) ABSTRACT

A spinal midline indicator (10) has a body (14) of radiolucent material for insertion between adjacent vertebrae (18, 20) and a radiographic marker (12) located centrally with the body to indicate the position of the spinal midline (22) in anterior-posterior images when the body is centrally located between the vertebrae. The radiographic marker is typically an elongate metal handle. The body may carry secondary radiographic markers (16) on opposite sides of and equidistant from the handle so that the handle indicates the position of the spinal midline when the body is placed centrally between the vertebrae.

11 Claims, 2 Drawing Sheets

U.S. PATENT DOCUMENTS

| | | |
|---|---|---|
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zuckerman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthan |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |

| Patent/Publication | Date | Inventor |
|---|---|---|
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,531,001 B2 | 5/2009 | de Villiers et al. |
| 7,637,913 B2 | 12/2009 | de Villiers et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Feree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Feree |
| 2006/0069439 A1 | 3/2006 | Zucherman et al. |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |

| | | | |
|---|---|---|---|
| 2007/0021837 A1 | 1/2007 | Ashman et al. | |
| 2007/0032875 A1 | 2/2007 | Blacklock et al. | |
| 2007/0061011 A1 | 3/2007 | de Villiers et al. | |
| 2007/0067035 A1 | 3/2007 | Falahee | |
| 2007/0067036 A1 | 3/2007 | Hudgins et al. | |
| 2007/0073398 A1 | 3/2007 | Fabian et al. | |
| 2007/0093898 A1 | 4/2007 | Schwab et al. | |
| 2007/0100453 A1 | 5/2007 | Parsons et al. | |
| 2007/0100454 A1 | 5/2007 | Burgess et al. | |
| 2007/0100456 A1 | 5/2007 | Dooris et al. | |
| 2007/0123903 A1 | 5/2007 | Raymond et al. | |
| 2007/0123904 A1 | 5/2007 | Stad et al. | |
| 2007/0135923 A1 | 6/2007 | Peterman et al. | |
| 2007/0162133 A1 | 7/2007 | Doubler et al. | |
| 2007/0168033 A1 | 7/2007 | Kim et al. | |
| 2007/0168036 A1 | 7/2007 | Ainsworth et al. | |
| 2007/0179615 A1 | 8/2007 | Heinz et al. | |
| 2007/0213821 A1 | 9/2007 | Kwak et al. | |
| 2007/0233077 A1 | 10/2007 | Khalili | |
| 2007/0233247 A1 | 10/2007 | Schwab | |
| 2007/0233248 A1 | 10/2007 | Schwab et al. | |
| 2007/0233251 A1 | 10/2007 | Abdou | |
| 2007/0270970 A1 | 11/2007 | Trieu | |
| 2007/0282449 A1 | 12/2007 | de Villiers et al. | |
| 2007/0299521 A1 | 12/2007 | Glenn et al. | |
| 2008/0015698 A1 | 1/2008 | Marino et al. | |
| 2008/0015701 A1 | 1/2008 | Garcia et al. | |
| 2008/0021557 A1 | 1/2008 | Trieu | |
| 2008/0051900 A1 | 2/2008 | de Villiers et al. | |
| 2008/0051901 A1 | 2/2008 | de Villiers et al. | |
| 2008/0125864 A1 | 5/2008 | de Villiers et al. | |
| 2008/0133011 A1 | 6/2008 | de Villiers et al. | |
| 2008/0154301 A1 | 6/2008 | de Villiers et al. | |
| 2008/0154382 A1 | 6/2008 | de Villiers et al. | |
| 2008/0215155 A1 | 9/2008 | de Villiers et al. | |
| 2008/0221696 A1 | 9/2008 | de Villiers et al. | |
| 2008/0228274 A1 | 9/2008 | de Villiers et al. | |
| 2008/0228277 A1 | 9/2008 | de Villiers et al. | |
| 2008/0294259 A1 | 11/2008 | de Villiers et al. | |
| 2009/0043391 A1 | 2/2009 | de Villiers et al. | |
| 2009/0048674 A1 | 2/2009 | Zubok et al. | |
| 2009/0048677 A1 | 2/2009 | McLeod et al. | |
| 2009/0076614 A1 | 3/2009 | Arramon | |
| 2009/0105833 A1 | 4/2009 | Hovda et al. | |
| 2009/0105834 A1 | 4/2009 | Hovda et al. | |
| 2009/0105835 A1 | 4/2009 | Hovda et al. | |
| 2009/0222101 A1 | 9/2009 | de Villiers et al. | |
| 2009/0276051 A1 | 11/2009 | Arramon et al. | |
| 2010/0004746 A1 | 1/2010 | Arramon | |
| 2010/0016972 A1 | 1/2010 | Jansen et al. | |
| 2010/0016973 A1 | 1/2010 | de Villiers et al. | |
| 2010/0069976 A1 | 3/2010 | de Villiers et al. | |

FOREIGN PATENT DOCUMENTS

| | | |
|---|---|---|
| DE | 10035182 A1 | 7/2002 |
| EP | 0 333 990 A2 | 9/1989 |
| EP | 0 560 140 A1 | 9/1993 |
| EP | 0 560 141 A1 | 9/1993 |
| EP | 0 591 712 A1 | 4/1994 |
| EP | 0 820 740 | 1/1998 |
| EP | 1 142 544 A1 | 10/2001 |
| EP | 1 153 582 A2 | 11/2001 |
| EP | 1 250 898 A1 | 10/2002 |
| EP | 1 306 064 A1 | 5/2003 |
| EP | 1 344 493 A1 | 9/2003 |
| EP | 1 344 506 A1 | 9/2003 |
| EP | 1 344 507 A2 | 9/2003 |
| EP | 1 344 508 A3 | 9/2003 |
| EP | 1 405 615 A1 | 4/2004 |
| EP | 1 417 940 A1 | 5/2004 |
| EP | 1 570 813 | 9/2005 |
| FR | 2 803 741 | 7/2001 |
| JP | 61-122859 | 6/1986 |
| JP | 63-164948 | 7/1988 |
| JP | 01-136655 | 5/1989 |
| JP | 06-007391 | 1/1994 |
| JP | 2002-521090 T | 7/2002 |
| JP | 2003-508119 T | 3/2003 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 01/01893 A1 | 1/2001 |
| WO | WO 01/15637 | 3/2001 |
| WO | WO 01/68003 A1 | 9/2001 |
| WO | WO 02/11650 | 2/2002 |
| WO | WO 04/000170 | 12/2003 |
| WO | WO 04/000171 | 12/2003 |
| WO | WO 2004/026187 A1 | 4/2004 |
| WO | WO 2004/054477 | 7/2004 |
| WO | WO 2005/004756 A2 | 1/2005 |
| WO | WO 2005/004756 A3 | 1/2005 |
| WO | WO 2005/053580 A1 | 6/2005 |
| WO | WO 2005/072662 | 8/2005 |
| WO | WO 2005/112834 | 12/2005 |
| WO | WO 2006/119092 A2 | 11/2006 |
| WO | WO 2006/119092 A3 | 11/2006 |
| WO | WO 2007/121320 | 10/2007 |
| ZA | 03/9312 | 11/2003 |

OTHER PUBLICATIONS

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439 (2000).

Lehuec et al., "Shock Absorption in Lumber Disc Prosthesis," *Journal of Spinal Disorders & Techniques*, vol. 16, No. 4, pp. 346-351(2003).

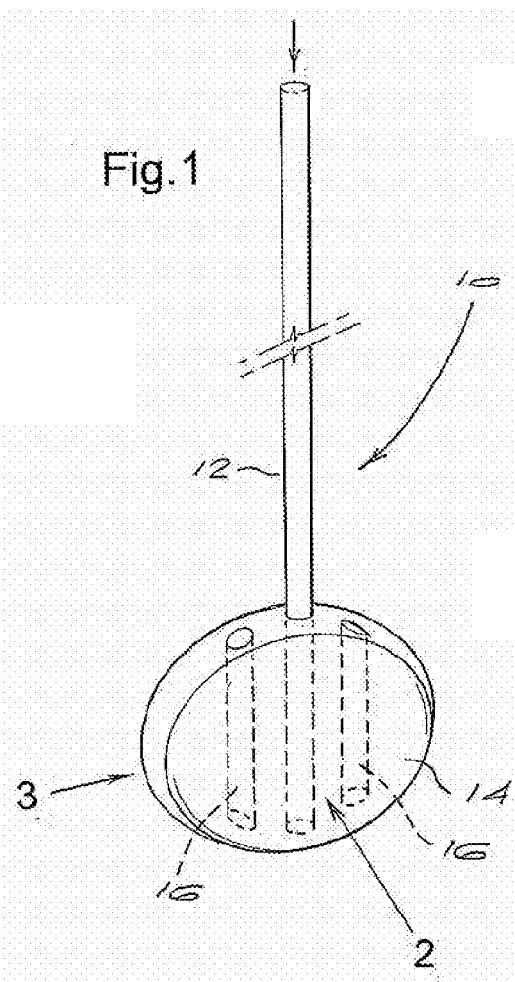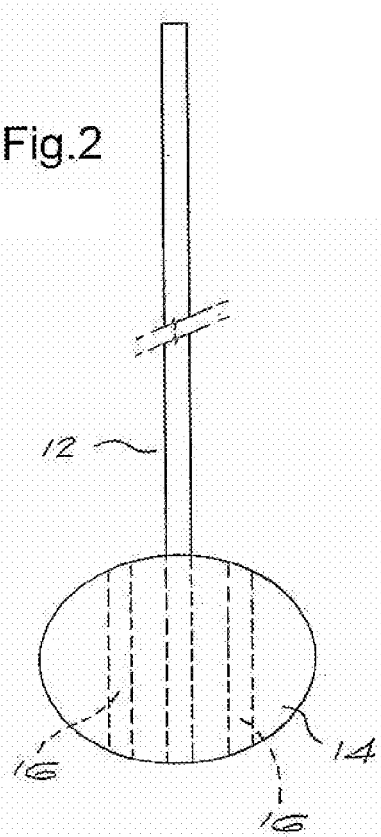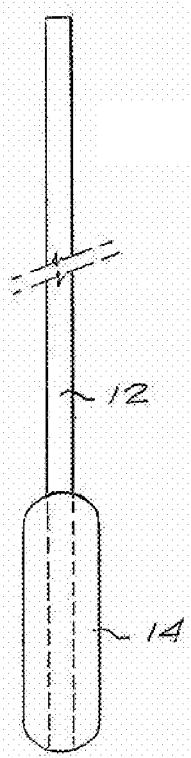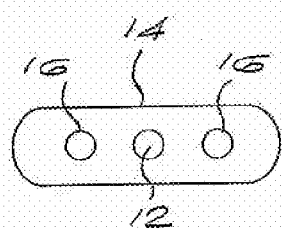

SPINAL MIDLINE INDICATOR

CROSS-REFERENCES TO RELATED APPLICATIONS

This application is a continuation of U.S. Ser. No. 11/187,733 filed Jul. 21, 2005, which application is a continuation of International Application PCT/IB2004/000170 filed on Jan. 26, 2004, which claimed priority from South African application 2003/0874 filed on Jan. 31, 2003; the full disclosures, each of which are incorporated herein by reference in their entirety.

BACKGROUND OF THE INVENTION

This invention relates to a spinal midline indicator.

It is important for a surgeon performing an ALIF (anterior lumbar interbody fusion) or ACIF (anterior cervical interbody fusion) cage or spinal disc replacement procedure to be able accurately to establish the centre- or midline of the spine. It is only once the surgeon has correctly established the position of the spinal midline that he is able to place the cage or spinal disc accurately on that midline. ff-centre placement will result in eccentric loading and possible early failure or accelerated wear.

At present, surgeons attempt to establish the spinal midline by visual inspection of an A-P (anterior-posterior) image. However this is often inaccurate, and can lead to subsequent off-centre placement of the cage or disc with potential disadvantages as described above.

The present invention seeks to provide an instrument which will facilitate accurate establishment of the spinal midline.

BRIEF SUMMARY OF THE INVENTION

According to the present invention there is provided a spinal midline indicator comprising a body of radiolucent material for insertion between adjacent vertebrae and a radiographic marker associated centrally with the body to indicate, in an anterior-posterior radiographic image, the position of the spinal midline when the body is appropriately located between the vertebrae. Conveniently the radiographic marker is an elongate handle which is connected to the body to facilitate placement of the body between the vertebrae and which is made of a radiographic material, i.e., a material which is substantially opaque to radiographic (fluoroscopic) imaging.

In the preferred embodiment, the body carries, in addition to the handle which serves as a first radiographic marker, two or more secondary radiographic markers on opposite sides of and equidistant from the first marker, whereby the first marker indicates the position of the spinal midline when the body is placed centrally between the vertebrae and the secondary markers are seen in the radiographic image to be equidistant from lateral edges of the vertebrae.

Further according to the invention there is provided a method of identifying a spinal midline which comprises the steps of inserting the body of a spinal midline indicator as summarized above between adjacent spinal vertebrae, manipulating the body so that the radiographic marker is seen in a radiographic image to be on the spinal midline, and, using the position of the radiographic marker as a guide, applying a marking, eg. a pin, to a vertebra to indicate the midline.

Other features of the invention are set forth in the appended claims.

BRIEF DESCRIPTION OF THE DRAWINGS

The invention will now be described in more detail, by way of example only, with reference to the accompanying drawings.

FIG. 1 shows a perspective view of a spinal midline indicator according to the invention;

FIG. 2 shows a side view of the indicator in the direction of the arrow 2 in FIG. 1;

FIG. 3 shows a side view of the indicator in the direction of the arrow 3 in FIG. 1;

FIG. 4 shows an end view of the indicator in the direction of the arrow 4 in FIG. 1;

DETAILED DESCRIPTION OF THE INVENTION

The spinal midline indicator 10 seen in FIGS. 1 to 4 includes an elongate handle 12 and a body 14 carried centrally at one end of the handle. The handle is made of a radiographic material, i.e. one which is opaque to radiation in the radiowave part of the spectrum, including X-radiation. The handle may, for instance, be made of stainless steel or titanium. The handle 12 extends substantially through the body 14. The body 14 is made of a radiolucent material, i.e. one which is at least to some degree transparent to the radiation. The body may, for instance, be made of PEEK (polyetheretherketone) or UHMWPE (ultra-high molecular weight polyethylene).

Embedded in the body 14 are two elongate markers 16, also of radiographic material such as stainless steel or titanium. The markers 16 are aligned parallel to the handle 12 and are located on opposite sides of, and equidistant from the handle.

Figure 5:
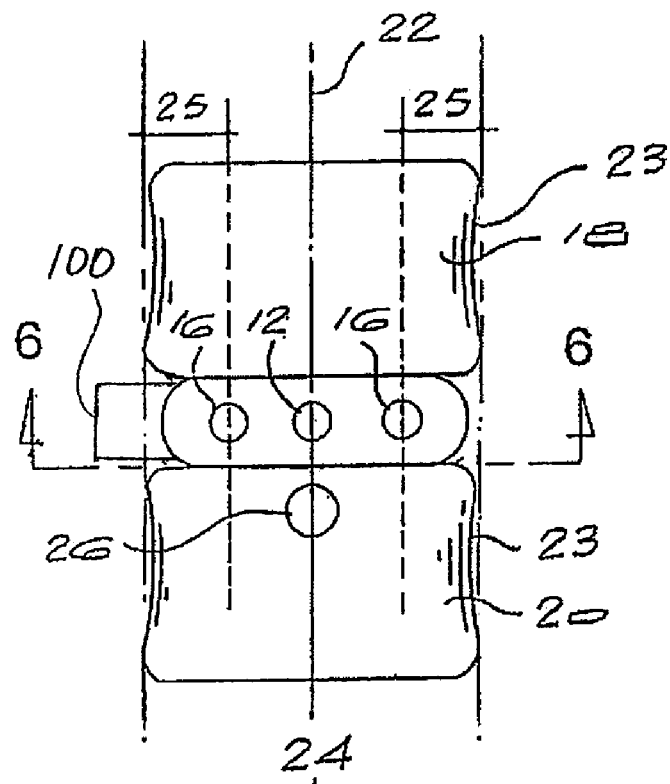
FIG. 5 diagrammatically illustrates the indicator in use.

FIG. 5 diagrammatically illustrates, in an anterior view, adjacent upper and lower vertebrae 18 and 20 respectively. As explained above it is important, during an ALIF or ACIF cage or spinal disc replacement procedure carried out anteriorly, for the surgeon to be able accurately to establish the spinal midline, indicated by the line 22, since it is centrally on this line that the replacement disc or cage must be placed. The procedure is typically carried out, with the patient lying prone and flat on his back, through a frontal incision.

In order to establish the midline 22, the surgeon aligns the handle 12 at a vertical orientation and uses it to insert the body 14 between the vertebrae 18 and 20. It will be understood that a separate instrument 100 is used to hold the vertebrae apart for this insertion to take place. An attempt is made to orientate the body centrally with the handle 12 vertical, thereby to ensure that the handle correctly indicates the midline 22.

An X-ray photograph or radiographic image is taken in the vertical anterior-posterior direction. In this radiographic image the handle 12, markers 16 and vertebrae 18,20 will be visible. By ensuring that the markers 16 are equidistantly laterally spaced from the osseous edges 23 of the vertebrae, i.e. that the distance 25 is the same on both sides, the surgeon can ensure that the body 14 and handle 12 are centrally positioned. It will be understood that during this procedure, the handle 12 itself operates as a radiographic marker indicating a central position.

It will also be understood that if the handle 12 and markers 16 are aligned with the anterior-posterior direction in which the radiographic image is taken, they will appear in the radiographic image merely as dots of small lateral dimension. However if the handle is not perfectly aligned in the anterior-posterior, i.e. vertical direction, parallax effects will result in the handle and markers being seen as lines rather than dots.

Figure 6:
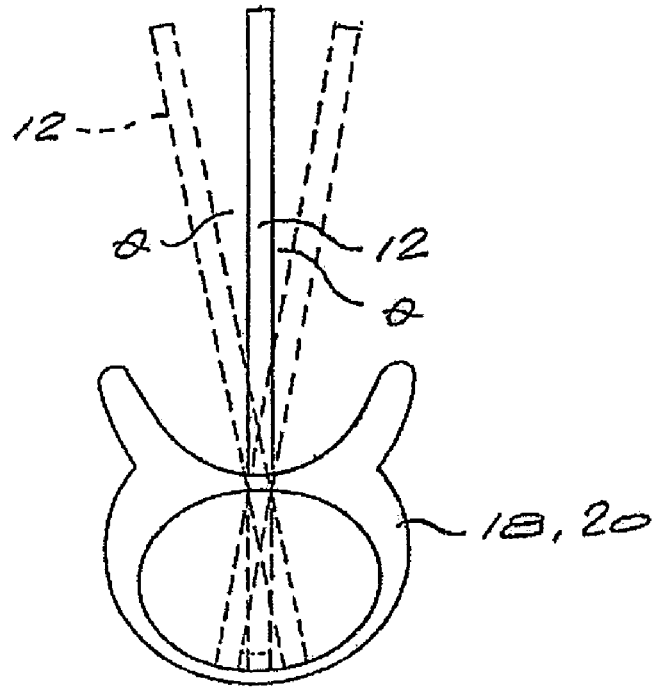
FIG. 6 shows a diagrammatic cross-section at the line 6-6 in FIG. 5.

This is illustrated in FIG. 6 in which the full lines show the handle 10 at the correct anterior-posterior or vertical orientation and the broken lines show it at orientations in which it is misaligned by an angle 9. It will be understood that in a radiographic image in the anterior-posterior direction indicated by the arrow 24, the handle 12 and markers 16 will appear as dots at the full line orientation but as short lines at the broken line orientations.

By consulting radiographic images and manipulating the indicator 10 as necessary in response to the information derived therefrom, the surgeon can ensure that the indicator is at the correct position and orientation. When the indicator is in the correct position and at the correct orientation, the handle 12 will lie in a vertical plane containing the midline 22. The surgeon can now use the handle as a positive indicator of that midline. The position of the radiographic marker can be used as a guide to apply a marking to a vertebra to indicate the midline. He can accurately mark the midline, for instance by knocking a pin 26 into one of the vertebrae.

Once the midline has been marked on one or both of the vertebrae, the indicator 10 is no longer required and can be removed for later re-use. The marker(s) then serve to indicate the midline 22 to enable subsequent, accurate positioning of the relevant prosthesis to take place.

What is claimed is:

1. A spinal midline indicator comprising:
    a body of radiolucent material sized and shaped to fit into an intervertebral space between two adjacent vertebrae; and
    a radiographic marker formed as an elongated handle attached to and extending from the body along a central axis of the body in an anterior-posterior direction and
    at least two secondary radiographic markers on opposite sides of the elongated handle and located equidistant from the elongate handle and from lateral edges of the body.

2. A spinal midline indicator according to claim 1, wherein the handle is made of stainless steel or titanium.

3. A spinal midline indicator according to claim 1, wherein the secondary radiographic markers are embedded in the body.

4. A spinal midline indicator according to claim 1, wherein the body has a length in a direction of the handle which is smaller than a width in a direction perpendicular to the length.

5. A spinal midline indicator according to claim 1, wherein the handle extends substantially through the body.

6. A spinal midline indicator to identify a spinal midline, the indicator comprising:
    a body of radiolucent material sized and shaped to fit into an intervetebral space between two adjacent vertebrae; and
    a radiographic marker centrally disposed within the body and extending from the body to guide a marking applied to the midline of at least one of the two adjacent vertebrae and
    at least two secondary radiographic markers on opposite sides of the elongated handle and located equidistant from the elongate handle and from lateral edges of the body.

7. A spinal midline indicator according to claim 6, further comprising a handle is made of stainless steel or titanium.

8. A spinal midline indicator according to claim 6, wherein the secondary radiographic markers are embedded in the body.

9. A spinal midline indicator according to claim 6, wherein the marker extends substantially through the body.

10. A spinal midline indicator according to claim 1, wherein a central axis of the body is equal distance from each of two lateral edges of the body.

11. A spinal midline indicator according to claim 9, wherein the radiographic marker is disposed equal distance from each of two lateral edges of the body.

* * * * *